United States Patent [19]

Damon, II

[11] 4,296,240
[45] Oct. 20, 1981

[54] SILACYCLOALKANE AMIDES

[75] Inventor: Robert E. Damon, II, Randolph, N.J.

[73] Assignee: Sandoz, Inc., East Hanover, N.J.

[21] Appl. No.: 143,262

[22] Filed: Apr. 24, 1980

[51] Int. Cl.³ .................... C07F 7/10; C07D 209/10
[52] U.S. Cl. .................................. 556/406; 424/181;
                                                  260/326.13 C; 260/326.13 B
[58] Field of Search ............... 556/406; 260/326.13 C

[56] References Cited
U.S. PATENT DOCUMENTS 3,927,057 12/1975 Takamizawa et al. ............. 556/406
4,104,295 8/1978 Klosowski et al. ................. 556/406

Primary Examiner—Paul F. Shaver
Attorney, Agent, or Firm—Gerald D. Sharkin; Richard E. Vila; Frederick H. Weinfeldt

[57] ABSTRACT

Anti-atherosclerotic agents of the formula:

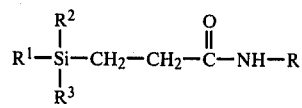

wherein $R^1$ is
(a) alkyl having from 1 to 22 carbon atoms; or
(b) of the formula

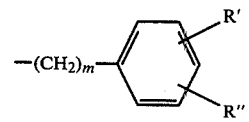

in which m is 0, 1 or 2, and each of R' and R" is, independently, hydrogen, halo or lower alkyl or alkoxy; $R^2$ and $R^3$ are joined to form with the silicon atom a heterocyclic ring having from 3 to 20 ring members; and R is an aralkyl-, phenyl- tryptophanyl- or benzocycloalkyl-type radical, eg 1-butyl-N-[(2-(4'-methyl-phenyl)-1-phenylethyl]-1-silacyclohexane propanamide, are obtained by reducing corresponding α,β-unsaturated analogs.

14 Claims, No Drawings

SILACYCLOALKANE AMIDES

This invention relates to silicon-bearing amides, and more particularly to a class of novel amides which bear a silacycloalkane moiety, novel intermediates in preparation of said class of amides, and the pharmaceutical use of said novel compounds and certain intermediates, as well as pharmaceutical compositions comprising said pharmaceutically useful novel compounds and intermediates.

The final compounds (I) which are obtainable by the process of this invention may conveniently be represented by the formula I:

$$R^1-\underset{\underset{R^3}{|}}{\overset{\overset{R^2}{|}}{Si}}-CH_2-CH_2-\overset{\overset{O}{\|}}{C}-NH-R \qquad I$$

wherein $R^1$ is either
(a) alkyl having from 1 to 22 carbon atoms; or
(b) of the formula $$-(CH_2)_m-\!\!\!\!\!\!\!\!\!\!\bigcirc\!\!\!\!\!\!\!\!\!\!\!\overset{R'}{\underset{R''}{}}$$

in which m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; $R^2$ and $R^3$ are joined to form with the silicon, a cyclic structure of from 3 to 20 ring members; and R is of type (a) an aralkyl-type radical of the structure $$-\underset{\underset{R^c}{|}}{\overset{}{CH}}-(CH_2)_g-\!\!\!\!\!\!\!\!\!\!\bigcirc\!\!\!\!\!\!\!\!\!\!\!\overset{R^a}{\underset{R^b}{}} \qquad (a)$$

wherein g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom;
subtype (ii) a radical of the structure $$-(CH_2)_p-\!\!\!\!\!\!\!\!\!\!\bigcirc\!\!\!\!\!\!\!\!\!\!\!\overset{y}{\underset{y'}{}} \qquad (ii)$$

in which p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms; or
R is of type (b) a phenyl-type radical of the structure $$\!\!\!\!\!\!\!\!\!\!\bigcirc\!\!\!\!\!\!\!\!\!\!\!\overset{R^b}{\underset{R^o}{}} \qquad (b)$$

in which $R^b$ is as defined above, and
$R^o$ is a hydrogen atom, halo having an atomic weight of from about 19 to 127, ie. alkoxy having from 1 to 4 carbon atoms, or alkyl having from 1 to 4 carbon atoms; or
$R^o$ is a radical of the structure $R^f$:

$$-(D)_f-\!\!\!\!\!\!\!\!\!\!\bigcirc\!\!\!\!\!\!\!\!\!\!\!-W$$

in which D is $-CH_2-$ or $-O-$;
f is 0 or 1; and
W is a hydrogen atom, halo having an atomic weight of from about 19 to 80, alkoxy having from 1 to 3 carbon atoms, or alkyl having from 1 to 3 carbon atoms; or
R is of type (c) an indolyl radical of the structure:

$$-\underset{\underset{COOR^4}{|}}{\overset{}{CH}}-CH_2-\!\!\!\!\!\!\!\!\!\!\underset{\underset{R^5}{|}}{\overset{3}{\underset{N}{\square}}}\!\!\!\!\!\!\!\!\!\!\overset{4\;\;5}{\underset{7\;\;6}{\bigcirc}}-R^b \qquad (c)$$

wherein $R^b$ is as defined above;
$R^4$ is alkyl having from 1 to 8 carbon atoms or benzyl; and
$R^5$ is a hydrogen atom, alkyl having from 1 to 8 carbon atoms or benzyl; or
R is (d) a benzocycloalkyl nucleus of the structure:

$$\underset{(CH_2)_j}{\square}\!\!\!\!\!\!\!\!\!\!\bigcirc\!\!\!\!\!\!\!\!\!\!\!\overset{y}{\underset{y'}{}} \qquad (d)$$

wherein y and y' are as defined above; and
j is a whole integer of from 1 to 4.

In the above-presented definition of Compounds I, halo having an atomic weight of from about 19 to 36, includes fluoro and chloro; halo having an atomic weight of from about 19 to 80 includes fluoro, chloro and bromo; while halo having an atomic weight of from about 19 to 127 includes fluoro, chloro, bromo and iodo. Exemplary of alkyl or alkoxy having from 1 to 3 or 1 to 4 carbon atoms is methyl, or methoxy and ethoxy. Unless otherwise indicated, alkyl and alkoxy may be branched or unbranched.

Particular embodiments of this invention are compounds I described above, and II, (hereinafter described), and intermediates thereof. The compounds and their intermediates may be viewed as falling into two-classes depending on whether $R^1$ is of type (a) or type (b). Additional subclasses are those in which $R^1$ is (of type a) alkyl having from 1 to 14 carbon atoms, such as n-butyl and n-decyl. Those compounds in which $R^1$ is of type (b) may be for example, phenyl or benzyl. It is also preferred that R is of type (a), particularly 2-(p-methylphenyl)-1-phenylethyl.

$R^2$ and $R^3$ are especially joined to form a saturated acyclic hydrocarbon radical forming with the silicon atom a heterocyclic ring having at least 3 but not more than 20 ring members and no more than 25 carbon atoms. Such hydrocarbon radical may be branched, typically by methyl or ethyl groups, particularly 1 or 2 methyl groups, but is conveniently unbranched and represented by a polymethylene chain, ie $-(CH_2)-$ which together with the silicon atom forms a cyclic structure; n being from 2 to 19, preferably from 2 to 13, particularly 2 to 7 and especially 4 or 5. It is also preferrd that the total number of carbon atoms in $R^1 + R^2 + R^3$ is not more than 35.

Further preferred forms of Compounds I when R is of type (a) or (b) and $R^o$ is not $R^f$, are that it is preferred that when $R^a$, $R^o$ or y is other than a hydrogen atom and $R^b$ (or y') is a hydrogen atom, that $R^o$, or $R^a$, or y be located at the 4-position; and that when $R^b$ (or y') is also other than a hydrogen atom that $R^a$ or $R^o$ and $R^b$ (or y and y') are the same, and it is additionally preferred that they be located at the 2- and 4-positions of the phenyl ring. When R is of type (a) where g=1, and $R^c$ is of type (ii) where p=0, then R can be an $\alpha$-(phenyl)-$\beta$-(p-methylphenyl) ethyl radical, and when $R^c$ is of type (ii) where p=1, then R can be an $\alpha$-(benzyl)-phenylethyl radical.

With particular respect to the substituent $R^o$ when it is a radical $R^f$, it will be appreciated that when $D=CH_2$ and f=1, then the radical $R^f$ is of the benzyl type. When D=oxygen and f=1, then the radical $R^f$ is of the phenoxy-type. When f=zero, then the radical $R^f$ is of the phenyl-type. Hence, when R is of type (b), and $R^o$ is of type $R^f$ where f=zero, then R can be a biphenylyl radical. The radical $R^f$ is preferably at the para-position. When W is other than a hydrogen atom, it is preferably at the para-position.

With respect to R, when it is of type (c), it is preferred that when $R^b$ is other than a hydrogen atom, it be located at the 5-position of the indole nucleus. It is also preferred that when $R^4$ is alkyl, it is unbranched, particularly ethyl.

With respect to R when it is of type (d) it is preferred that when y is other than a hydrogen atom, that it be located at a carbon atom ortho to the ring junction; and that when y' is also other than a hydrogen atom, it is preferred that it be the same as y, and it is additionally preferred that it be in para-relationship to y'. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

In the above-presented definitions, when $R^o$, $R^1$ or y is halo, it is preferably fluoro or chloro, and particularly chloro; and when $R^2$ or y' is halo it is preferably chloro.

The above-described compounds I are obtainable by reduction of corresponding ethylenically unsaturated silicon-bearing compounds of formula II:

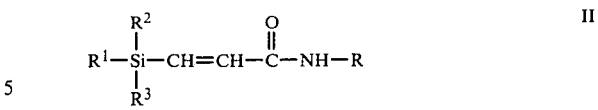

in which $R^1$, $R^2$, $R^3$, and R are as defined above (process a). Compounds I and II have pharmaceutical activity as is described hereinafter under the heading "Statement of Utility."

The above described compounds II are obtainable by reduction of corresponding alkynyl Compounds (III):

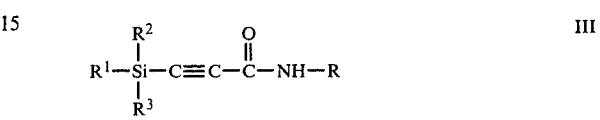

in which $R^1$, $R^2$, $R^3$ and R are as defined above (process b).

Process (b) may be accomplished by means conventionally employed in converting an alkynyl-bearing compound to its corresponding alkenyl-analog. A convenient method of carrying out process (b) is by treating a compound III with hydrogen in the presence of an appropriate catalyst such as palladium on calcium carbonate (eg 5%), or rhodium, platinum or platinum oxide, on such "controlling" porous supports as calcium carbonate, barium sulfate and the like, in an inert medium e.g. a lower alkanol such as ethanol, lower fatty acids and esters, such as acetic acid and ethyl acetate, hydrocarbons, such as benzene or toluene or a cyclic ether such as tetrahydrofuran (THF), at moderate temperatures, for example from about 10° to 80° C. particularly at from about 20° to 30° C., at moderate pressures, e.g. from about 15 to 100 psi (over atmospheric pressure), e.g. at 15 psi (over at.).

If desired Compounds III may be converted to their corresponding Compounds I (without recovery of any Compounds II formed during the process, i.e. process a') by means conventionally employed in reducing an alkynyl compound to its corresponding alkyl analog.

Processes (a) and (a') may be accomplished, for example, by hydrogenating under pressures of e.g., from about 15 psi to about 100 psi (all over atmospheric pressure), e.g. 50 psi in the presence of a catalyst such as platinum oxide or other hydrogenation catalysts mentioned in connection with process (b) above, or on active supports, such as charcoal, in an inert medium, such as ethyl acetate, or such media as mentioned in connection with the discussion of process (b) above, and at moderate temperatures, e.g. 10° to 100° C., particularly at from about 20° to 30° C.

It will be appreciated that by selection of such factors as catalyst, pressure of hydrogen, temperature, and reaction time, optimum yields of the desired compounds I or II may be obtained from corresponding Compounds III, since "total" hydrogenation of the starting alkynyl compound (III) will result in the formation of a corresponding Compound I, while controlled hydrogenation will give predominantly Compound II.

Compounds III are obtainable by reaction of a corresponding organo-metallo Compound of the formula IV:

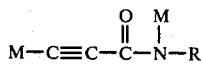

in which R is as defined above and M is an equivalent of an active metal eg an alkali metal or a magnesium halide with a halo-silane of the formula V:

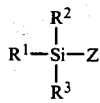

in which $R^1$, $R^2$ and $R^3$ are as defined, and Z is halo having an atomic weight of from about 19 to 127, i.e. fluoro, chloro, bromo or iodo, preferably chloro, (process c), to form an adduct which is then hydrolyzed (process c').

Process (c) is carried out under essentially anhydrous conditions, eg under an atmosphere of inert gas such as dry nitrogen, as are conventionally observed in carrying out Grignard-type reactions, at moderate temperatures, e.g. −40° to 0° C., in an aprotic medium, e.g. an ether such as tetrahydrofuran, dimethoxyethane, or a hydrocarbon such as benzene or toluene, which yields an adduct which corresponds to a compound III but in which the "amido" nitrogen atom bears an M-unit (M being as defined above) or a hydrolyzable silyl group corresponding to V, where an excess thereof is used.

The hydrolysis step (process c') may be accomplished in the conventional manner for hydrolyzing a Grignard-type adduct, by treatment with water or a dilute aqueous solution of a salt or acid, e.g., saturated aqueous ammonium chloride, at moderate temperatures e.g. from about 5° to 90° C., preferably at from about 20° to 30° C.

The above-described Compounds IV are obtainable by treatment of a corresponding propiolamide of the formula VI:

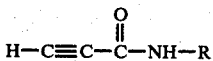

in which R is as defined above, with a M-contributing agent (process d).

Process (d) may be accomplished in the conventional manner for forming organo-metallic reagents by replacing acidic hydrogen atoms of an organic compound with active metal atoms. For example Compounds IV may be obtained by treating the free form of a Compound VI with at least 2 equivalents of M-contributing agent (VII) at reduced temperatures, for example Compounds VI and VII may be combined at about −78° to −20° C., e.g. −60° C., and held at low temperatures with agitation while they are reacting, e.g. at about −40° C. to 0° C., e.g. −20° C., in an aprotic medium, e.g. an ether, such as THF, dimethoxyethane, or a hydrocarbon, such as hexane, benzene or toluene. Since Compounds IV are decomposed by moisture, it is convenient to employ them directly in Process (c) without recovery, which could involve exposure to moist air, or to maintain them in a conventional stabilizing medium, such as the moisture-free inert aprotic media suitable for use in process (d).

In the M-contributing agents, (Compounds VII), M is an equivalent of an active metal, or a magnesium halide. Active metals include the alkali metals, i.e. lithium, sodium and potassium, lithium being preferred, while the halo portions of the magnesium halide may be chloro or bromo. A convenient lithium-contributing agent is lithium diisopropylamide (LDA) which may be prepared by reacting n-butyl lithium dissolved in an inert hydrocarbon, such as hexane, with an equivalent of diisopropylamine dissolved in an aprotic solvent, e.g. THF, at reduced temperatures such as at about −78° to +25° C., e.g. at −30° C., under essentially anhydrous conditions. It is convenient to prepare the reagent (VII) and use it in situ in process (d).

The above-described propiolamides (VI) are obtainable by amidation of propiolic acid, or an active derivative thereof, with an R-bearing primary amine of the formula IX:

$$H_2N-R \qquad IX$$

in which R is as defined above. A convenient method of carrying out such an amidation reaction is by reacting a mixed anhydride of propiolic acid of the formula VIII:

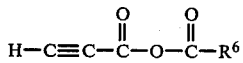

in which $R^6$ is lower alkyl having from 1 to 6 carbon atoms, e.g. ethyl, with a compound IX (process e). The desired compound VIII may be prepared and used in situ, by treating propiolic acid with an equivalent amount (or slight excess) of a non-nucleophilic base, e.g. an alkali hydride, such as lithium hydride or sodium hydride, or triethylamine, under essentially anhydrous conditions, in an aprotic medium, e.g. an ether, such as THF, or dimethoxyethane, a hydrocarbon such as benzene or toluene, or a halogenated hydrocarbon such as methylene chloride or chloroform, at moderate temperatures e.g. from about 0° to 30° C., preferably from about 20° to 25° C., then slowly introducing into the reaction mixture a chloroformate of the formula X:

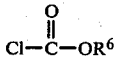

in which $R^6$ is as defined above, (process e'), at reduced temperatures, e.g. from about −20° to −5° C., preferably below 10° C., in an aprotic medium such as was used in preparing the reaction mixture, under essentially anhydrous conditions.

The desired amido compound (VI) may be conveniently obtained by slowly adding an amine (IX) to a mixed anhydride, in such aprotic media as described in connection with the preparation of the mixed anhydride (e.g. in situ) at reduced temperatures, e.g. from about −25° C. to 0° C., preferably at from about −15° to 0° C.

The above-described series of reactions may conveniently be represented by Reaction Scheme A, below in which R, $R^1$, $R^2$, $R^3$, $R^6$, Z and M are as defined above.

Reaction Scheme A

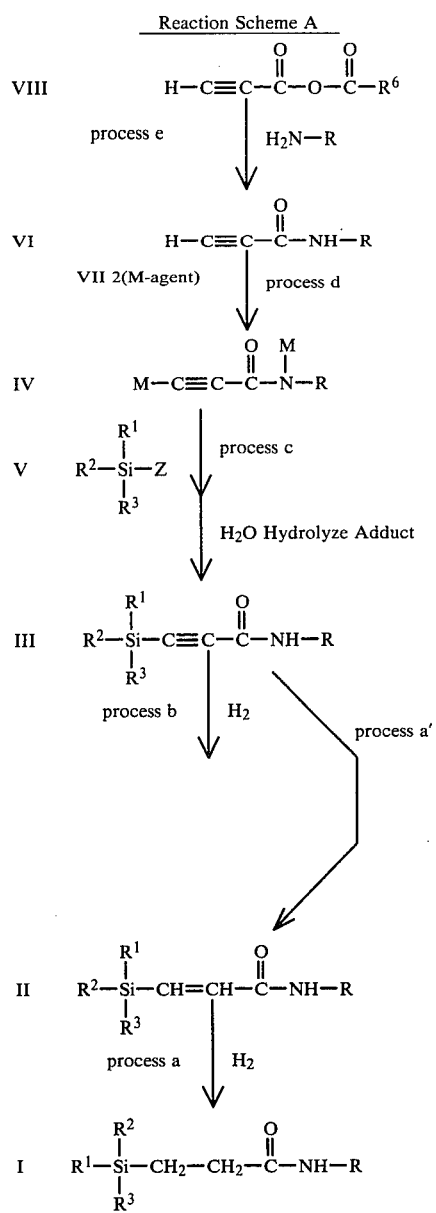

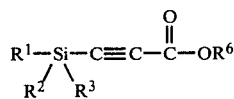

Various modifications of the above-described procedure for obtaining Compounds I and II are possible, and may be conveniently practiced, depending upon such factors as relative availability of starting materials and reagents, scale of production, ease of handling etc. For example, to obtain Compounds III, one may prepare silicon-bearing esters of the formula XI

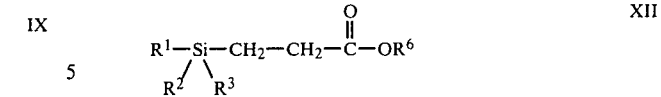

in which $R^1$, $R^2$, $R^3$ and $R^6$ are as defined above, and react such ester (or free acid form thereof), with an amino compound (IX), under conditions conventionally employed in preparing amides. Alternatively, the acetylenically unsaturated position of an ester compound (XI) as defined above, may be hydrogenated fully to obtain an ester of the formula XII

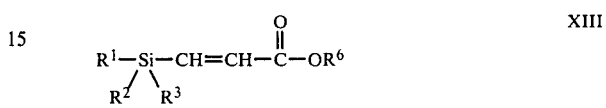

in which $R^1$, $R^2$, $R^3$ and $R^6$ are as defined above, and then reacted with an amine (IX) to obtain the corresponding final compound I; or partially hydrogenated to obtain a ethylenically unsaturated ester XIII:

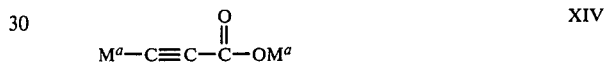

in which $R^1$, $R^2$, $R^3$ and $R^6$ are as defined above, which upon rection with an amine IX will yield the corresponding compound II.

An alternative method of preparing Compounds III is by reacting under essentially anhydrous conditions an active metal salt form of propiolic acid of the formula XIV:

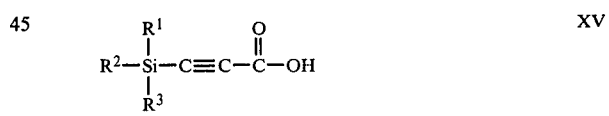

in which $M^a$ is an equivalent of active metal or magnesium halide, with a suitable tri-substituted halo silane (V, as described above) in connection with process (c), in an aprotic medium, at moderate temperatures, eg. 0° to 40°, preferably at 20° to 30° C. The same media may be used as mentioned in connection with process (c) to obtain a trisubstituted alkynoic acid compound of the formula XV

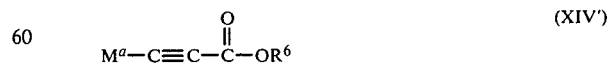

in which $R^1$, $R^2$ and $R^3$ are as defined above, which is then reacted with a suitable amine (IX) to obtain the corresponding compound III.

If desired, an ester form of propiolic acid may be employed in place of compound XIV, ie of the formula XIV'

$$M^a-C\equiv C-\overset{\overset{O}{\|}}{C}-OR^6 \qquad (XIV')$$

in which $M^a$ and $R^6$ are as defined above.

The above-described alternative procedures may be conveniently represented by Reaction Scheme B, below, in which $R^1$, $R^2$, $R^3$, $R^6$, R, Z, and $M^a$ are as defined above.

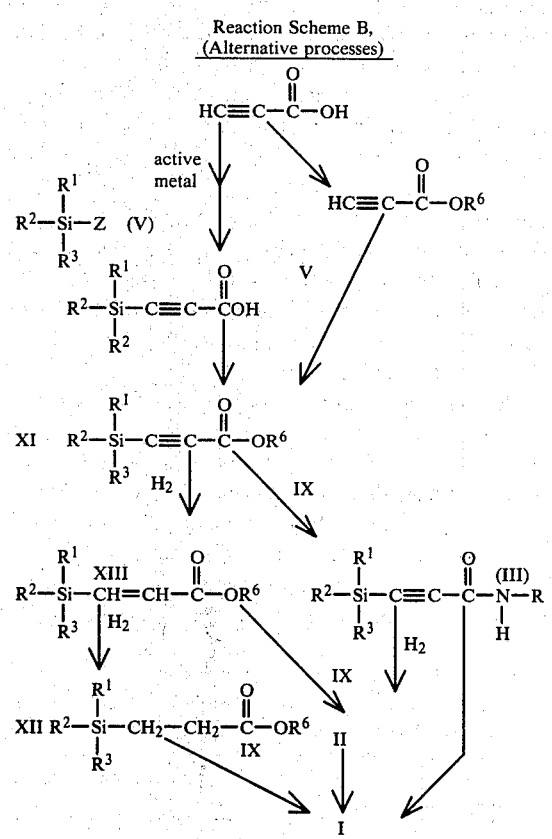

Reaction Scheme B,
(Alternative processes)

Recovery of the intermediates and products obtained by the above-described procedures may be effected by conventional techniques, such as crystallization, precipitation, vacuum distillation, and chromatographic techniques such as column or thin layer chromatography and the like.

It will be understood that many compounds of this invention, eg I, II and III, may exist in the form of stereoisomers, eg optically active isomers, ie enantiomers, which can be prepared from respective stereoisomers, eg optically active compounds IX or separated and recovered by conventional techniques, eg resolution and such isomeric forms are also included within the scope of this invention.

Many of the reagents and compounds involved in the above-described procedures are known, eg propiolic acid and compounds v and IX, and may be obtained commercially or may be prepared by methods described in the literature, while those compounds not specifically described in the literature may be prepared by analogous methods from known starting materials.

STATEMENT OF UTILITY

The compounds of formulas I and II of this invention are useful as pharmaceutical agents in animals. In particular, the compounds I and II are useful in controlling the cholesterol ester content of mammalian arterial walls and are therefore particularly indicated for use as antiatherosclerotic agents, ie. agents useful in the prophylactic treatment of atherosclerosis and in the controlling of atherosclerotic conditions due to cholesterol ester accumulation in the arterial walls. Such ability of the compounds I and II are indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg. aorta, wall) obtained by the method of K. Fisher-Dzoga et al (Experimental and Molecular Pathology 18, 162–176 (1973)) are routinely grown in 75 cm$^2$ tissue culture flasks using Minimum Essential Medium (Eagle) supplemented with 10% fetal bovine serum. For testing a 75 cm$^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the meethod of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

| Composition of Reagents for Cholesterol Determination | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxphenylacetic acid | .15 | mg/ml |
| C. Sodium Hydroxide Solution | .5N | |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds I and II are administered at a daily dosage of from about 0.2 milligrams to about 500 milligrams per kilogram of animal body weight, preferably given in divided doses two to four times a day, or in sustained release form. For most large mammals, the total daily dosage is from about 10 milligrams to about 5,000 milligrams preferably from about 10 milligrams to 2,000 milligrams. Dosage forms suitable for internal use comprise from about 2.5 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

A representative formulation for administration orally three times a day prior to feeding in the treatment of atherosclerosis is a gelatin capsule prepared by conventional techniques to contain the following

| Ingredient | Weight (in mg.) |
|---|---|
| 1-butyl-N-[2-(p-methyl-phenyl)- 1-phenylethyl]-1-silacyclohexane propanamide | 250 |
| corn oil | 500 |

As is the present understanding in the art, controlling the total cholesterol content of an arterial wall by inhibiting the accumulation thereof by reducing the cholesterol ester content thereof, advantageously inhibits the formation of plaques in the arterial wall.

Compounds I and II are also indicated as agents for the lowering of blood serum cholesterol and cholesterol ester levels, and hence also further indicated as antiatherosclerotic agents by feeding tests in rabbits eg at 200 mg/kg of test compound per day for 9 weeks, in conjunction with a high cholesterol diet resulting in, compared to controls, a reduction in cholesterol and cholesterol ester blood serum levels, as well as a lessened formation or absence of arterial wall plaques.

The following examples of the preparation of intermediates and compounds I and II of the invention are illustrative of the invention. All temperatures are centigrade (°C.) and room temperature is 20° to 30° C. unless indicated otherwise.

EXAMPLE 1

1-butyl-N-[(1'-phenyl-2'-p-tolyl)ethyl]-1-silacyclohexane propanamide (a compound I)

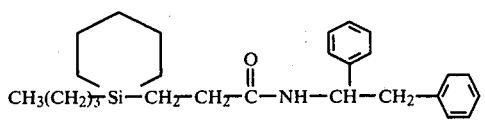

Step A: N-[(1'-phenyl-2'-p-tolyl)-ethyl]-propiolamide

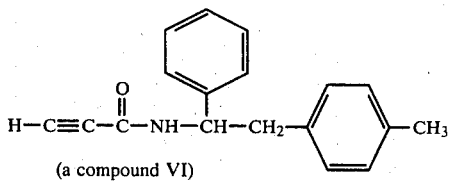

(a compound VI)

95 mg of lithium hydride are added to a solution of 850 mg propiolic acid in 15 ml of freshly distilled THF*, portion-wise, over a period of about 45 min., with cooling to avoiding heating over room temperature (hydrogen evolves). The resulting mixture is then cooled to about −10°, and a solution of 1.3 g of ethyl chloroformate in 3 ml of dry THF is added drop-wise with stirring, while maintaining the temperature below −10°. The resulting mixture is then stirred for 2 hrs. at about −15°. A solution of 2.5 g of (1-phenyl 2-p-tolyl) ethylamine** in 5 ml of dry THF is then added dropwise at from −15° to 0°, with stirring. The mixture is then stirred at room temperature for 2 hours.

*tetrahydrofuran
**also known as 2-(4'-methylphenyl)-1-phenylethylamine

The reaction mixture is concentrated by evaporation in vacuo (solvent stripped) to obtain a residue, which is taken up in methylene chloride and is washed first with dilute aqueous sodium bicarbonate, then with dilute hydrochloric acid, then dried over anh. sodium sulfate, and concentrated in vacuo to obtain crude product. The crude product of this example is refined by crystallizing from diethyl ether m.p. 152°–155° C.

Step B: n-butyl-cychopentamethylene-chlorosilane

In a separate vessel, under nitrogen, to a solution of 800 mg of cyclopentamethylenedichlorosilane in 10 ml of dry THF, is added a solution of 290 mg of n-butyl lithium in 2.9 ml of dry hexane at a temperature of from about −10° to −16° with stirring. The mixture is continued stirring at room temperature for 30 min. and held for use in step C.

Step C: 1-butyl-N-[(1'-phenyl-2'-p-tolyl)-ethyl]-1-silacyclohexane-1-propynamide a Compound III)

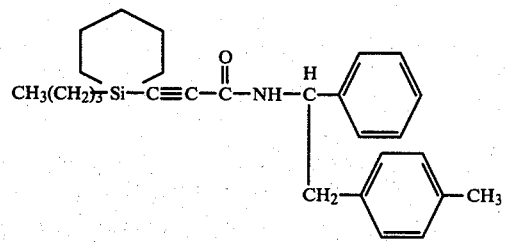

In a vessel, under an atmosphere of dry nitrogen at −30° a solution of 580 mg of n-butyl lithium in 5.8 ml of dry hexane is added to 900 mg of diisopropylamine in 10 ml of dry THF. The mixture stirred for 15 min., then cooled to −60°. A solution of 1.29 g of [(1'-phenyl-2'-p-tolyl)-ethyl]propiolamide in 10 ml of dry THF is added dropwise thereto while the temperature of the mixture is maintained between about −40° and −50°. The mixture is then stirred for 1 hr. at −25°. The solution of n-butyl-pentamethylenechlorosilane prepared in step B is added dropwise, with stirring while maintaining the temperature at below about −10° and the mixture stirred for 3 hr. (at −20°).

Aqueous saturated ammonium chloride is added to the reaction mixture, and the organic phase recovered, dried over anh. sodium sulfate, and concentrated by evaporation in vacuo to obtain the crude product as an oil, which is refined by eluting through a silica gel column using chloroform as eluate to yield the product of this step as an oil, which crystallizes on standing to a solid (m.p. 87°–90°).

Step D: 1-butyl-N-[(1'-phenyl-2'-p-tolyl)-ethyl]-1-silacyclohexane propanamide (a Compound I)

To a solution of 1 g 1-butyl-N-[(1'-phenyl-2'-p-tolyl)-ethyl]1-silacyclohexane-1-propynamide in 1 liter of ethyl acetate in a hydrogenating apparatus, is added 300 mg of platinum oxide, and a pressure of 50 p.s.i. hydrogen is maintained for 24 hours with shaking. The reaction mixture is then filtered, and the filtrate concentrated (by evaporation in vacuo) to obtain the title product as an oil.

EXAMPLE 2

1-Butyl-N-[(1'-phenyl-2'-p-tolyl)-ethyl]-1-silacyclohexane-1-propenamide (a Compound II)

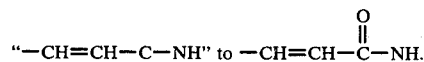

To a solution of 300 mg of 1-butyl-N-[(1'-phenyl-2'-p-tolyl)-ethyl]-silacyclohexane-2-propynamide in 30 ml of ethanol in a hydrogenating apparatus, is added 50 mg of 5% palladium on calcium carbonate. The mixture is placed under 1 at. pressure of hydrogen and shaken until an equivalent of hydrogen gas had been taken up (about 45 min.). The reaction mixture is then filtered, and the filtrate concentrated (by evaporation in vacuo) to obtain the title product.

EXAMPLE 3

1-Butyl-N-[(1'-phenyl-2'-p-tolyl)-ethyl]-silacyclohexane-1-propanamide

Treating 1-butyl-N-[(1'-phenyl-2'-p-tolyl)-ethyl]-silacyclohexane 1-propenamide (obtained by Example 2) by the procedure of Step D of Example 1, the title product is obtained.

EXAMPLE 4

Repeating the procedure of steps (A), (B) and (C) of Example 1, but using in place of the (1-phenyl-2-p-tolyl-)ethylamine used in Step (A), therein, an approximately equivalent amount of the following amines as compounds IX:

(a) 1-amino-indane;
(b) DL-tryptophan ethyl ester, hydrochloride;
(c) (d,1) α-methylbenzylamine; (racemate);
(d) 2-methylaniline; or
(e) 1-benzyl-2-phenylethylamine: there is accordingly obtained, respectively (as compounds III):
(a) 1-butyl-N-(1'-indanyl)-1-silacyclohexane-1-propynamide;
(b) 1-(4'-sila-4',4'-pentamethylene-n-octoyl)-tryptophan, ethyl ester;
(c) 1-butyl-N-(α-methylbenzyl)-1-silacyclohexane-1-propynamide; (as a racemic mixture);
(d) 1-butyl-N-(o-methylphenyl)-1-silacyclohexane-1-propynamide; and
(e) 1-butyl-N-(1'-benzyl-2'-phenylethyl)-1-silacyclohexane-1-propynamide;
which upon treatment by the method of Step (D) of Example 1 yield the corresponding compounds I, or by treatment by the method of Example 2 yield the corresponding compounds II which upon treatment by the method of Step (D) of Example 1, then, yield the corresponding compounds I.

EXAMPLE 5

Following the general procedure of steps (A), (B), and (C) of Example 1, but using in place of the n-butyl-silapentamethylenechlorosilane used in step (C) therein, an approximately equivalent amount of the following compounds V (which may be prepared in a manner analogous to that of step B of Example 1):
(a) 1-butyl-tetramethylenechlorosilane
(b) 1-butyl-hexamethylenechlorosilane;
(c) 1-n-decyl-pentamethylenechlorosilane;
(d) 1-n-decyl-tetramethylenechlorosilane;
(e) 1-methyl-pentamethylenechlorosilane;
(f) 1-butyl-undecamethylenechlorosilane;
(g) 1-benzyl-pentamethylenechlorosilane;
(h) 1-phenyl-pentamethylenechlorosilane; or
(i) 1-butyl 1-chloro-4-methyl-silacyclohexane;
there is accordingly obtained, respectively (as Compounds III):
(a) 1-butyl-N-[(1'-phenyl-2'-p-tolyl)ethyl]-silacyclopentane-1-propynamide;
(b) 1-butyl-N-[(1'-phenyl-2'-p-tolyl)ethyl]-silacycloheptane-1-propyamide;
(c) 1-n-decyl-N-[(1'-phenyl-2'-p-tolyl)ethyl]-silacyclohexane-1-propynamide;
(d) 1-n-decyl-N-[(1'-phenyl-2'-p-tolyl)ethyl]-silacyclopentane-1-propynamide;
(e) 1-methyl-N-[(1'-phenyl-2'-p-tolyl)ethyl]-silacyclohexane-1-propynamide;
(f) 1-butyl-N-[(1'-phenyl-2'-p-tolyl)ethyl]-silacyclodecane-1-propynamide;
(g) 1-benzyl-N-[(1'-phenyl-2'-p-tolyl)ethyl]-silahexane-1-propynamide;
(h) 1-phenyl-N-[(1'-phenyl-2'-p-tolyl)ethyl]-silahexane-1-propynamide; and
(i) 1-butyl-4-methyl-N-[(1'-phenyl-2'-tolyl)ethyl]-silahexane-1-propyamide.

EXAMPLE 6

Repeating the procedure of step (D) of Example 1, but using in place of the 1-butyl-N-[(1'-phenyl-2'-p-tolyl)-ethyl]silacyclohexane-1-propenamide used therein, an approximatly equivalent amount of each of the products (a) to (i) of Example 5, there is accordingly obtained, respectively, the corresponding compounds I:
(a) 1-butyl-N-[(1'-phenyl-2'-p-tolyl)-ethyl]-silacyclopentane propanamide;
(b) 1-butyl-N-[(1'-phenyl-2-p-tolyl)-ethyl]-silacycloheptane propanamide;
(c) 1-n-decyl-N-[(1'-phenyl-2-p-tolyl)-ethyl]-silacyclohexane propanamide;
(d) 1-n-decyl-N-[(1'-phenyl-2'-p-tolyl)-ethyl]-silacyclopentane-propanamide;
(e) 1-methyl-N-[(1'-phenyl-2'-p-tolyl)-ethyl]-silacyclohexane propanamide;
(f) 1-butyl-N-[(1'-phenyl-2'-p-tolyl)ethyl]-silacyclodecane-propanamide.
(g) 1-benzyl-N-[(1'-phenyl-2'-p-tolyl)ethyl]-silacyclohexane propanamide;
(h) 1-phenyl-N-[(1'-phenyl-2'-p-tolyl)ethyl]-silacyclohexane propanamide; and
(i) 1-butyl-4-methyl-N-[(1'-phenyl-2'-p-tolyl)ethyl]-silacyclohexane propanamide.

EXAMPLE 7

Repeating the procedure of Example 2, but using in place of the 1-butyl-N-[(1'-phenyl-2'-p-tolyl)-ethyl]-silacyclohexane-1-propynamide used therein, an approximately equivalent amount of each of the products (a) to (i) of Example 5, there is accordingly obtained, respectively, the corresponding compounds II:
(a) 1-butyl-N-[(1'-phenyl-2-p-tolyl)-ethyl]-sila-cyclopentane-1-propenamide;
(b) 1-butyl-N-[(1'-phenyl-2-p-tolyl)-ethyl]-silacycloheptane-1propenamide;
(c) 1-n-decyl-N-[(1'-phenyl-2-p-tolyl)-ethyl]-silacyclohexane-1-propenamide;
(d) 1n-decyl-N-[(1'-phenyl-2'-p-tolyl)-ethyl]-sila-cyclopentane-1-propenamide.
(e) 1-methyl-N-[(1'-phenyl-2'-p-tolyl)-ethyl]-silacyclohexane-1-propenamide;
(f) 1-butyl-N-[(1'-phenyl-2'-p-tolyl)ethyl]-sila-cyclododecane-1-propenamide;
(g) 1-benzyl-N-[(1'-phenyl-2'-p-tolyl)ethyl]-sila-hexane-1-propenamide; and
(h) 1-phenyl-N-[(1'-phenyl-2'-p-tolyl)ethyl]-silacyclohexane-1-propenamide;
(i) 1-butyl-4-methyl-N-[(1'-phenyl-2'-p-tolyl-)ethyl]-silacyclohexane propenamide;
which upon treatment by the procedure of Step (D) of Example 1 yield the corresponding compounds I, ie compounds (a) to (i) of Example 6.

What is claimed is:
1. A compound of the formula:

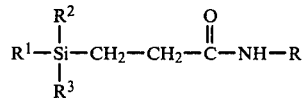

wherein R¹ is either
(a) alkyl having from 1 to 22 carbon atoms; or
(b) of the formula

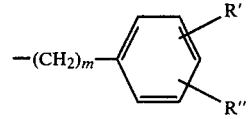

in which
m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127;
R² and R³ are joined to form an acyclic hydrocarbon radical which together with the silicon atom forms a ring having from 3 to 20 ring members and having no more than 25 carbon atoms; and
R is of type (a) an aralkyl-type radical of the structure

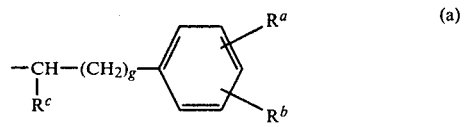

(a)

wherein g is 0, 1 or 2;

$R^a$ is a hydrogen atom, halo having an atomic weight of from about 19 to 127, alkoxy having from 1 to 4 carbon atoms, or alkyl having from 1 to 4 carbon atoms, or trifluoromethyl;

$R^b$ is a hydrogen atom, alkyl having from 1 to 3 carbon atoms, alkoxy having from 1 to 3 carbon atoms, or halo having an atomic weight of from about 19 to 36; and $R^c$ is subtype (i) a hydrogen atom; subtype (ii) a radical of the structure

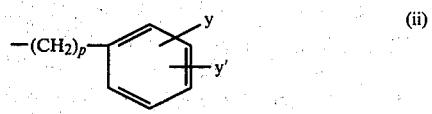     (ii)

in which p is 0, 1 or 2, and y is a hydrogen atom, halo having an atomic weight of from about 19 to 127, alkoxy having from 1 to 4 carbon atoms, or alkyl having from 1 to 4 carbon atoms; and y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms; or R is of type (b) a phenyl-type radical of the structure

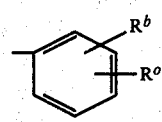     (b)

in which $R^b$ is as defined above, and $R^o$ is a hydrogen atom, halo having an atomic weight of from about 19 to 127, ie. alkoxy having from 1 to 4 carbon atoms, or alkyl having from 1 to 4 carbon atoms; or $R^o$ is a radical of the structure $R^f$:

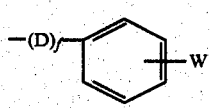

in which

D is —CH$_2$— or —O—;

f is 0 or 1; and

W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

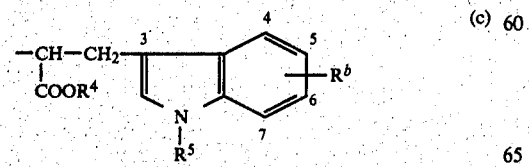     (c)

wherein $R^b$ is as defined above;

$R^4$ is alkyl having from 1 to 8 carbon atoms or benzyl; and $R^5$ is a hydrogen atom, alkyl having from 1 to 8 carbon atoms or benzyl; or R is (d) a benzocycloalkyl nucleus of the structure:

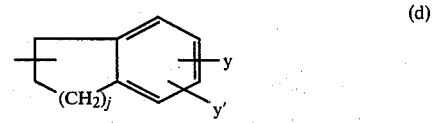     (d)

wherein y and Y' are as defined above; and j is a whole integer of from 1 to 4.

2. A compound of claim 1 in which $R^1$ is of type (a).
3. A compound of claim 1 in which $R^1$ is of type (b).
4. A compound of claim 1 in which R is of type (a).
5. A compound of claim 1 in which R is of type (b).
6. A compound of claim 1 in which R is of type (c).
7. A compound of claim 1 in which R is of type (d).
8. A compound of claim 1 in which $R^2$ and $R^3$ are joined to form a —(CH$_2$)—$_n$ radical in which n is a whole number of from 2 to 19.
9. A compound of claim 7 in which n is 5.
10. A compound of claim 1 in which $R^1$ is n-butyl.
11. A compound of claim 1 in which R is (1-phenyl-2-p-tolyl)ethyl.
12. The compound of claim 1 which is 1-butyl-N-[(1'-phenyl-2'-p-tolyl)ethyl]-1-silacyclohexane propanamide.
13. A compound of the formula:

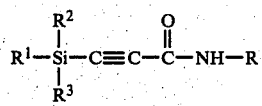

wherein $R^1$ is either (a) alkyl having from 1 to 22 carbon atoms; or (b) of the formula

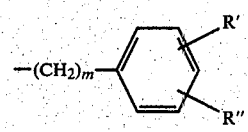

in which m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127;

$R^2$ and $R^3$ are joined to form an acyclic hydrocarbon radical which together with the silicon atom forms a ring having from 3 to 20 ring members and no more than 25 carbon atoms; and R is of type (a) an aralkyl-type radical of the structure

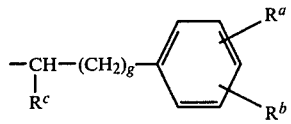 (a)

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii) a radical of the structure

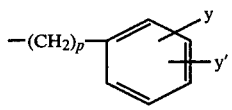 (ii)

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or
subtype (iii) alkyl having from 1 to 8 carbon atoms; or
R is of type (b) a phenyl-type radical of the structure

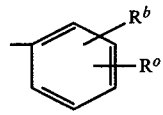 (b)

in which
$R^b$ is as defined above, and
$R^o$ is a hydrogen atom, halo having an atomic weight of from about 19 to 127, ie. alkoxy having from 1 to 4 carbon atoms, or alkyl having from 1 to 4 carbon atoms; or
$R^o$ is a radical of the structure $R^f$:

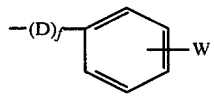

in which
D is —CH₂— or —O—;
f is 0 or 1; and
W is a hydrogen atom, halo having an atomic weight of from about 19 to 80, alkoxy having from 1 to 3 carbon atoms, or alkyl having from 1 to 3 carbon atoms; or
R is of type (c) an indolyl radical of the structure:

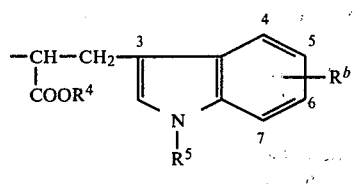 (c)

wherein
$R^b$ is as defined above;
$R^4$ is alkyl having from 1 to 8 carbon atoms or benzyl; and
$R^5$ is a hydrogen atom, alkyl having from 1 to 8 carbon atoms or benzyl; or
R is (d) a benzocycloalkyl nucleus of the structure:

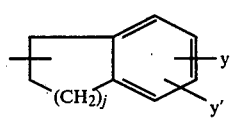 (d)

wherein
y and y' are as defined above; and
j is a whole integer of from 1 to 4.

14. A compound of the formula:

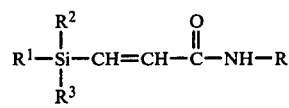

wherein
$R^1$ is either
(a) alkyl having from 1 to 22 carbon atoms; or
(b) of the formula

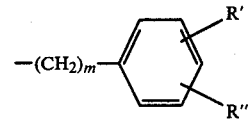

in which
m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127;
$R^2$ and $R^3$ are joined to form an acyclic hydrocarbon radical which together with the silicon atom form a ring having from 3 to 20 ring members and having no more than 25 carbon atoms; and
R is of type (a) an aralkyl-type radical of the stucture

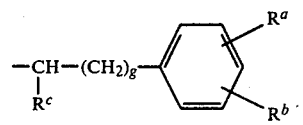 (a)

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;

$R^b$ is a hydrogen atom, alkyl having from 1 to 3 carbon atoms, alkoxy having from 1 to 3 carbon atoms, or halo having an atomic weight of from about 19 to 36; and $R^c$ is subtype (i) a hydrogen atom; subtype (ii) a radical of the structure

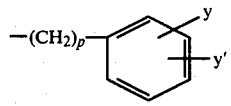 (ii)

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or
subtype (iii) alkly having from 1 to 8 carbon atoms; or
R is of type (b) a phenyl-type radical of the structure

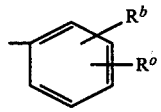 (b)

in which
$R^b$ is as defined above, and
$R^o$ is a hydrogen atom, halo having an atomic weight of from about 19 to 127, ie. alkoxy having from 1 to 4 carbon atoms, or alkyl having from 1 to 4 carbon atoms; or $R^o$ is a radical of the structure $R^f$:

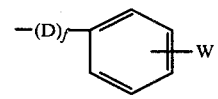

in which
D is $—CH_2—$ or $—O—$;
f is 0 or 1; and
W is a hydrogen atom, halo having an atomic weight of from about 19 to 80, alkoxy having from 1 to 3 carbon atoms, or alkyl having from 1 to 3 carbon atoms; or
R is of type (c) an indolyl radical of the structure:

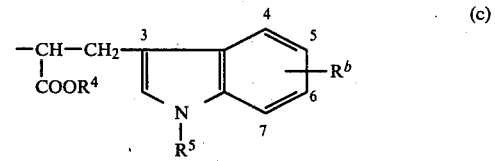 (c)

wherein
$R^b$ is as defined above;
$R^4$ is alkyl having from 1 to 8 carbon atoms or benzyl; and
$R^5$ is a hydrogen atom, alkyl having from 1 to 8 carbon atoms or benzyl; or
R is (d) a benzocycloalkyl nucleus of the structure:

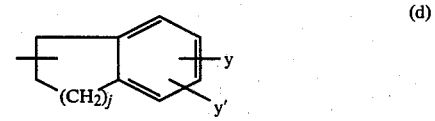 (d)

wherein
y and y' are as defined above; and
j is a whole integer of from 1 to 4.

* * * * *